United States Patent [19]

Katsuro et al.

[11] Patent Number: 5,258,530
[45] Date of Patent: Nov. 2, 1993

[54] PROCESS FOR PRODUCING BIPHENYLTETRACARBOXYLIC DIANHYDRIDE

[75] Inventors: Yoshio Katsuro; Hitoshi Matsuda, both of Fukuoka, Japan

[73] Assignee: Mitsubishi Kasei Corporation, Tokyo, Japan

[21] Appl. No.: 18,188

[22] Filed: Feb. 16, 1993

[30] Foreign Application Priority Data

Feb. 18, 1992 [JP] Japan ............................ 4-30816

[51] Int. Cl.$^5$ ............................................ C07D 307/89
[52] U.S. Cl. ................................................ 549/241
[58] Field of Search .................................... 549/231

[56] References Cited

U.S. PATENT DOCUMENTS 3,145,237  8/1964  Van Helden et al. ............ 585/427
3,940,426  2/1976  Itatani et al. ..................... 549/241

OTHER PUBLICATIONS

Chemical Abstracts, vol. 80, No. 5, Feb. 4, 1974, Abstract No. 26963x.

*Primary Examiner*—Bernard Dentz
*Attorney, Agent, or Firm*—Sughrue, Mion, Zinn, Macpeak & Seas

[57] ABSTRACT

A process for producing a biphenyltetracarboxylic dianhydride which comprises the step of: heating phthalic anhydride at a temperature of from 135° to 300° C. in the presence of a palladium catalyst thereby to allow the phthalic anhydride to undergo a dimerization reaction. According to the process, biphenyltetracarboxylic dianhydride can be synthesized by the direct dimerization of phthalic anhydride.

7 Claims, No Drawings

PROCESS FOR PRODUCING BIPHENYLTETRACARBOXYLIC DIANHYDRIDE

FIELD OF THE INVENTION

The present invention relates to a process for producing a biphenyltetracarboxylic dianhydride (hereinafter referred to as "BPDA"). More particularly, this invention relates to a novel process for producing a BPDA by the direct dimerization of phthalic anhydride.

BACKGROUND OF THE INVENTION

BPDAs are attracting attention as monomers for use in producing polyimides, which are heat-resistant resins. Conventionally known methods for synthesizing BPDA include, for example, a process in which a phthalic diester, e.g., dimethyl o-phthalate, is subjected to a dimerization reaction in the presence of both a palladium catalyst and a molecular oxygen to produce a tetramethyl biphenyltetracarboxylate (as described, e.g., in JP-B-62-17564), and this compound is hydrolyzed into a biphenyltetracarboxylic acid, which is then dehydrated into a BPDA (as described, e.g., in JP-A-1-104063 and U.S. Pat. No. 4,958,002)). (The terms "JP-B" and "JP-A" as used herein mean an "examined Japanese patent publication" and an "unexamined published Japanese patent application," respectively.)

Also known is a process in which a halogenated phthalic acid, e.g., 4-chlorophthalic acid obtained by chlorinating phthalic acid, is subjected to a dimerization reaction in an aqueous solution containing an alkali as a halogen acceptor in the presence of a reducing agent and a specific palladium catalyst, thereby to produce a biphenyltetracarboxylic acid, which is then dehydrated to synthesize a BPDA (as described, e.g., in JP-A-2-53742).

However, these processes are disadvantageous in that they necessitate many reaction steps and complicated treating procedures before the desired BPDA is obtained. Therefore, it is extremely troublesome to practice the processes industrially, and the overall yield of the desired BPDA is not always high.

For these reasons, there has been a demand for a synthesizing method of a BPDA that is industrially advantageous and in that the number of reaction steps required is small. For example, if a BPDA can be produced directly from phthalic anhydride by dimerization, the treating procedure can be greatly simplified. However, there have so far been no reports concerning the direct dimerization of phthalic anhydride. It has been thought that this may be because the anhydride bond in phthalic anhydride reacts with catalysts to inhibit the dimerization reaction.

SUMMARY OF THE INVENTION

An object of the present invention is to provide a novel process for the synthesis of biphenyltetracarboxylic dianhydride (BPDA).

Other objects and effects of the present invention will be apparent from the following description.

As a result of the intensive studies made by the present inventors concerning the direct dimerization reaction of phthalic anhydride, it has surprisingly been found that when phthalic anhydride is allowed to react under specific conditions in the presence of a palladium catalyst, it undergoes a direct dimerization reaction to directly give a BPDA and the reaction proceeds without causing the phthalic anhydride to turn into the dicarboxylic acid.

The present invention provides a process for producing a biphenyltetracarboxylic dianhydride (BPDA) which comprises the step of: heating phthalic anhydride at a temperature of from 135° to 300° C. in the presence of a palladium catalyst thereby to allow the phthalic anhydride to undergo a dimerization reaction.

DETAILED DESCRIPTION OF THE INVENTION

In the present invention, a BPDA is produced directly from phthalic anhydride by heating it in the presence of a palladium catalyst. The temperature for this reaction is from 135° to 300° C., preferably from 180° to 280° C., and more preferably from 250° to 280° C. If the reaction temperature is too low, a BPDA is not formed satisfactorily. Too high reaction temperatures are not preferred in that volatilization of the phthalic anhydride, as starting material, and the yielded BPDA occurs.

It is generally preferred in the reaction according to the present invention that a solvent as a third ingredient is not used and that additional phthalic anhydride in excess of the amount for dimerization is used, which functions as a solvent in a molten state. Since phthalic anhydride is in its molten state at any temperature within the range of the reaction conditions, it functions as a solvent. The amount of phthalic anhydride to be added can be determined according to the reaction conditions, e.g., the reaction temperature, the amount of catalyst, and the like.

In the reaction of the present invention, other solvent may also be used. As the solvent, any one may be employed as long as it dissolves phthalic anhydride and does not react with the anhydride bond in phthalic anhydride. Examples thereof include acetic acid, trifluoroacetic acid, acetic anhydride, and dimethylacetamide. The weight of the solvent to be used is usually from 0.2 to 50 times by weight, preferably from 1 to 20 times, the weight of the starting material.

The reaction according to the present invention may be carried out at substantially ordinary pressure, but if the boiling point of the solvent employed is lower than the reaction temperature, the reaction may be conducted at an elevated pressure.

Examples of the palladium catalyst include palladium salts of organic acids such as aliphatic carboxylic acids having from 1 to 5 carbon atoms, e.g., palladium formate, palladium acetate, palladium propionate, palladium butyrate, and palladium valerate; palladium salts of inorganic acids, e.g., palladium nitrate and palladium chloride; and complexes obtained by reacting these salts with o-phenanthroline, bipyridyl or the like. Among these, palladium salts of organic acids are preferred, with palladium acetate being especially preferred.

The amount of the palladium catalyst to be used is generally from 0.01 to 0.5 mol, preferably from 0.1 to 0.4 mol, in terms of the amount of palladium per mol of the phthalic anhydride. If the amount of the palladium catalyst used is too small, the dimerization reaction of phthalic anhydride tend not to proceed efficiently. Too large palladium catalyst amounts are disadvantageous in an economical standpoint.

The dimerization reaction according to the present invention can usually be practiced by introducing predetermined amounts of phthalic anhydride and a palladium catalyst and, if necessary, a solvent into a reaction vessel equipped with a stirrer, heating the resulting mixture to a desired reaction temperature, and maintaining the mixture at that temperature with stirring. Although the reaction time varies depending on the reaction temperature and other factors, it is generally about from 0.5 to 20 hours. It is preferred that the gas-phase part in the reaction vessel is replaced with an inert gas, e.g., nitrogen and carbon dioxide, before the reaction is performed. It is further preferred that the reaction is conducted while an inert gas is kept being passed through the gas-phase part to remove any volatile substance resulting from the reaction.

The reaction mixture after completion of the dimerization reaction mainly contains unreacted phthalic anhydride and a BPDA yielded. The palladium and palladium compounds present in the reaction system may first be removed by a conventionally known technique, for example, by causing these to be adsorbed onto active carbon and filtering out the resulting active carbon at a high temperature. Subsequently, the phthalic anhydride remaining unreacted may be removed by distillation thereby to obtain the intended BPDA.

The BPDA obtained by the present invention usually is a mixture of biphenyl-3,3',4,4'-tetracarboxylic dianhydride (hereinafter referred to as "S-isomer") and biphenyl-2,3,3',4'-tetracarboxylic dianhydride (hereinafter referred to as "$\alpha$-isomer"), with the proportion of the former to the latter isomer being, for example, from 1/1,000 to 1,000/1 by mole.

The thus-obtained BPDA may be separated into the above-mentioned isomers (S-isomer and $\alpha$-isomer) by a conventional technique or may be subjected to a purification treatment, according to the properties required of the intended product.

The present invention will be explained below in more detail with reference to the following examples, but the invention is not construed as being limited thereto.

EXAMPLE 1

Into a 100-ml three-necked flask were introduced 20 g (135 mmol) of phthalic anhydride and 6 g (27 mmol) of palladium acetate. The contents were then heated to 280° C. with stirring, and the phthalic anhydride was allowed to react for 5 hours in a nitrogen gas stream while acetic acid formed with the progress of the reaction was kept being distilled off from the reaction system. After the reaction, the reaction mixture was analyzed by liquid chromatography. As a result, the yield of BPDAs was 20.0% (S-isomer: 12.5%; $\alpha$-isomer: 7.5%).

EXAMPLE 2

Reaction was conducted in the same manner as in Example 1 except that the reaction temperature was changed to 250° C. As a result, the yield of BPDAs was 12.9% (S-isomer: 7.6%; $\alpha$-isomer: 5.2%).

EXAMPLE 3

Reaction was conducted in the same manner as in Example 1 except that the reaction temperature was changed to 200° C. As a result, the yield of BPDAs was 3.0% (S-isomer: 1.1%; $\alpha$-isomer: 1.9%).

COMPARATIVE EXAMPLE 1

20 g (135 mmol) of phthalic anhydride was heated at 80° C. for 5 hours in the same manner as in Example 1 except that palladium acetate was omitted. As a result, a BPDA was not formed.

While the invention has been described in detail and with reference to specific embodiments thereof, it will be apparent to one skilled in the art that various changes and modifications can be made therein without departing from the spirit and scope thereof.

What is claimed is:

1. A process for producing a biphenyltetracarboxylic dianhydride which comprises the step of: heating phthalic anhydride at a temperature of from 135° to 300° C. in the presence of a palladium catalyst thereby to allow said phthalic anhydride to undergo a dimerization reaction.

2. A process as claimed in claim 1, wherein said phthalic anhydride is used in an excess amount and said dimerization reaction is conducted substantially without a solvent as a third ingredient while maintaining said phthalic anhydride in a molten state.

3. A process as claimed in claim 1, wherein said palladium catalyst is a palladium salt of an organic acid.

4. A process as claimed in claim 1, wherein said palladium catalyst is used in an amount of from 0.01 to 0.5 mol in terms of the amount of palladium per mol of said phthalic anhydride.

5. A process as claimed in claim 1, wherein the temperature of said dimerization reaction is in the range of from 180° to 280° C.

6. A process as claimed in claim 1, wherein said dimerization reaction is conducted at substantially ordinary pressure.

7. A process as claimed in claim 1, wherein said dimerization reaction is conducted in a reaction vessel while an inert gas is kept being passed through a gas-phase part in said reaction vessel.

* * * * *